United States Patent [19]

Alt et al.

[11] Patent Number: 4,719,920

[45] Date of Patent: Jan. 19, 1988

[54] EXERCISE-RESPONSIVE RATE-ADAPTIVE CARDIAC PACEMAKER

[75] Inventors: Eckhard Alt, Munich, Fed. Rep. of Germany; Richard V. Calfee, Houston, Tex.

[73] Assignee: Intermedics, Inc., Angleton, Tex.

[21] Appl. No.: 917,558

[22] Filed: Oct. 10, 1986

[30] Foreign Application Priority Data

Nov. 25, 1985 [DE] Fed. Rep. of Germany ....... 3541598

[51] Int. Cl.$^4$ .............................................. A61N 1/36
[52] U.S. Cl. .............................. 128/419 PG; 128/736
[58] Field of Search ......................... 128/419 PG, 736

[56] References Cited

U.S. PATENT DOCUMENTS

| | | | |
|---|---|---|---|
| 3,867,950 | 2/1975 | Fischell | 128/419 PG |
| 4,527,568 | 7/1985 | Rickards | 128/419 PG |
| 4,543,954 | 10/1985 | Cook et al. | 128/419 PG |

FOREIGN PATENT DOCUMENTS

| | | | |
|---|---|---|---|
| 0133828 | 3/1985 | European Pat. Off. | 128/419 PG |
| 2609365 | 9/1977 | Fed. Rep. of Germany | 128/419 PG |
| 8505279 | 12/1985 | World Int. Prop. O. | 128/419 PG |

*Primary Examiner*—William E. Kamm
*Attorney, Agent, or Firm*—Leitner, Greene & Christensen

[57] ABSTRACT

A temperature driven rate responsive cardiac pacemaker adapted to distinguish between physiologically determined changes of the patient's blood temperature under conditions of exercise and non-exercise, and to adaptively vary the rate at which stimuli are generated accordingly, is also capable of recognizing the blood temperature dip which is characteristic of the commencement of exercise. In response to such a temperature dip, the pacemaker initiates a rapid and physiologically beneficial increase in the stimulation rate. To assure the proper selective initiation of a rate increase, the pacemaker discriminates between a blood temperature drop indicative of the onset of exercise and those temperature drops which occur for other reasons, such as upon cessation of exercise or as normal phasic variations, including respiration and circadian fluctuations.

18 Claims, 4 Drawing Figures

EXERCISE-RESPONSIVE RATE-ADAPTIVE CARDIAC PACEMAKER

BACKGROUND OF THE INVENTION

1. Field of the Invention

The present invention relates generally to cardiac pacemakers, and more particularly to an exercise-responsive implantable cardiac pacemaker in which the stimulation rate is adaptively regulated in part according to the central venous blood temperature of the patient.

2. Relevant Background

In situations where the natural pacemaker or pacing system of a patient's heart is disturbed because of age, disease or injury, it is customary to employ artificial pacing with an implanted cardiac pacemaker.

In the prior German patent No. 34 19 439 of Eckhard Alt, and corresponding application for U.S. patent Ser. No. 747,111, copending with and assigned to the same assignee as is the present application, a pacing rate-adaptive circuit for a cardiac pacemaker is disclosed in which the stimulation rate is controlled according to the central venous blood temperature of the patient and to the variation of blood temperature commensurate with one or the other of two different types of characteristic curves. These curves functionally describe the relationship between heart rate and central venous blood temperature, one of the curves being representative of a resting state of the patient and referred to as the basic curve (reference or resting function), and other curves being representative of exercise states of the patient and referred to as exercise curves or functions. The exercise curves are superimposed on the basic curve, each of the former having a higher slope than the latter and each intersecting the basic curve at a different reference temperature point. The stimulation rate of the cardiac pacemaker is controlled according to either the resting function or an exercise function depending on both (1) the the time rate of change of blood temperature relative to a threshold value preselected as the criterion for distinguishing between states of rest and exercise, and (2) the instantaneous blood temperature.

In the apparatus described in the aforementioned copending Alt application, the stimulation rate of the pacemaker is controllably varied in the same direction as the variation of blood temperature. Thus, a rise of blood temperature produces an increase in heart rate, and a drop of blood temperature results in a decrease in heart rate. When the patient is in an initial state of rest, which may include sleeping, reclining, sitting or standing without significant accompanying physical activity, the pacing rate is variably regulated under the control of the resting function based on then-current blood temperature level and the determination that the time rate of change of blood temperature lies below the preselected threshold value. When the patient commences physical activity sufficient to cause his central venous blood temperature to rise at a rate exceeding the threshold value, that condition is detected and results in a shift of pacing rate control from the reference function to that exercise function appropriate to the instantaneous level of his blood temperature.

In U.S. Pat. No. 4,436,092 to Cook et al., issued Mar. 13, 1984, a cardiac pacemaker is disclosed in which the stimulation rate is varied according to a single mathematical function derived from an observed relationship between blood temperature and heart rate for a normally functioning heart under stress. According to Cook, et al., various constants in the exercise algorithm representing this relationship were derived principally from experimental data on test dogs. The algorithm is used in conjunction with the output voltage wave of a temperature sensor to control the output repetition frequency of the pacemaker's pulse generator. A similar description is also given by Csapo et al. in the German patent OS No. 26 09 365, and in their paper entitled "Autoregulation of Pacemaker Rate by Blood Temperature" presented at the VIII World Congress of Cardiology in Tokyo, Japan in September 1978, as well as by a publication in Verh. Dtsch. Ges. Kreislaufforsch. 44:1978, page 152, entitled "Frequenzsteuerung von Schrittmachern durch Bluttemperatur." In the Cook et al. U.S. Pat. No. 4,436,092, the controlled variation of stimulation rate, and thus of the patient's heart rate, is also in the same direction as the change of the patient's central venous blood temperature, albeit the variation is limited to a single mathematical function.

Subsequent Cook et al. U.S. Pat. No. 4,543,954, issued Oct. 1, 1985, describes a pair of embodiments of an exercise responsive stimulation rate controlled cardiac pacemaker. In one embodiment, the stimulation rate is set at either of two discrete levels, one of which is a resting rate and the other an exercise rate. In another embodiment, three discrete settings are available, one of which is intermediate the other two. In both, an abrupt "either-or" type of shift between rates occurs in each direction based on whether or not the time derivative of blood temperature is respectively more positive or more negative than preselected set points, in contrast to normal physiological changes of heart rate. Again, the change in stimulation rate is in a direction consistent with that of the change of blood temperature.

In fact, however, the rise of blood temperature does not occur at the instant the physical exertion begins; rather, it is time delayed relative to the latter. At commencement of exercise, the central venous blood temperature typically dips, that is, drops slightly, owing to the rapid circulation of initially relatively cooler blood from the extremities to the heart. The heart temperature gradient of blood in the human body decreases in the direction from the heart to the periphery of the body. At the onset of physical exercise, there is increased circulation not only in the working musculature but also in the extremities. The lower temperature of the extremities initially tends to cool the blood flowing through them, for at least a brief interval of time.

Indeed, in individuals with below normal cardiac output, maintenance of sufficient blood circulation through the life-sustaining organs, such as the liver, kidneys and brain, is assured at the expense of lower circulation of the extremities and skin. Thus, patients with abnormal heart function experience lower temperature in the extremities than do persons with normally functioning hearts. This tends to compound the duration and extent of the blood temperature dip at the commencement of physical exercise in cardiac patients.

The temperature drop continues until the heat generated by the working muscles balances out the colder blood inflow from the extremities, thereby causing the central venous blood temperature to cease dropping and, with continued exercise, to rise. The extent and duration of this initial temperature dip depends on the functional state of the heart and circulatory system, the skin temperature and level of initial amount of exertion by the individual. In general, for persons with normal circulation in a state of rest, and who are clothed and not cool, the blood temperature drop may last from about twenty to about thirty seconds. As noted above, the duration of the drop may be considerably greater for persons with below normal blood circulation.

The initial exercise-prompted blood temperature drop has been reported in the literature; by Bundin in the Scan. J. Clin. Lab. Invest., 35, 1975, page 542, and with more recent results, by E. Alt et al. in the Journal Herzschrittmacher, Munich, 5 (1985), No. 2, page 66 et seq.

Accordingly, exercise-responsive cardiac pacemakers in which the stimulation rate is based on blood temperature typically will undergo a time delayed response to exercise, or even a drop of pacing rate at onset of exercise. This would appear to be the case, for example, with the regulation apparatus disclosed in the aforementioned Cook et al. patents. The exercise responsive pacemaker disclosed in the aforementioned copending Alt application has a stimulation rate controlled by the basic (resting) curve of heart rate as a function of central venous blood temperature, in a manner that will lead to only a slight decrease in the stimulation rate with the initial temperature drop according to regulation along the basic curve. On the other hand, it has been observed that for healthy persons the initiation of physical exertion is accompanied by an elevation of the heart rate, despite the dip in blood temperature. Therefore, it would be desirable to provide an exercise-responsive cardiac pacemaker which is controlled in a manner that the initial dip in blood temperature is detected, to trigger an adjustment of the stimulation rate corresponding to the heart rate of a healthy person with good cardiovascular circulation undergoing similar physical exercise at that blood temperature level.

It is a principal object of the present invention to provide an improved implantable cardiac pacemaker in which there is rapid recognition of the onset of exercise to produce a short term variation of pacing rate closely paralleling the heart rate of a normal healthy person under the same conditions.

Another object of the present invention is to develop criteria for use in detecting the initial drop of blood temperature as a reliable indicator of the onset of exercise to trigger an increased stimulation rate.

A further important object of the invention is to provide means to distinguish the initial drop of blood temperature attributable to the commencement of exercise from other situations in which the patient's central venous blood temperature may experience a short term drop, such as occurs following the completion of physical exercise.

SUMMARY OF THE INVENTION

The present invention provides a temperature driven rate responsive cardiac pacemaker which is implemented not only to distinguish between the physiologically determined changes of blood temperature occurring when the patient is in a resting state and those occurring when the patient is undergoing exercise, and to adaptively vary the stimulation rate of the pacemaker based on the time rate of change of blood temperature according to either of at least two markedly different relationships between heart rate and blood temperature, the selection of which depends on whetCher or not the temperature change is attributable to exercise; but also to recognize the dip in the blood temperature that normally occurs at the beginning of exercise, and thereupon to initiate a rapid and physiologically suitable compensatory elevation of the stimulation rate. Importantly, a pacemaker according to the invention discriminates between this decrease in the blood temperature and other situations where a temperature decrease is observed, to avoid responding with the exercise onset-induced type of rate adjustment in the latter situations.

According to a feature of the invention, the stimulation rate is maintained at the elevated level until such time as the longer term relationship between heart rate and blood temperature, represented by an exercise curve, is a more appropriate function for controlling stimulation rate. At that time, the control is shifted to the exercise curve function.

The rate adaptive pacemaker of the present invention is automatically triggered to the higher stimulation rate immediately upon detecting that the following criteria are fulfilled:

1. The pacemaker is functioning, and its stimulation rate is controlled, according to a functional relationship between heart rate and blood temperature representing the resting state of the patient. This criterion assures that the patient is not then exercising and has not just completed exercise, and hence, that a detected decrease of central venous blood temperature is not a post-exercise decrease.

2. The absolute drop ($\Delta T$) of the patient's central venous blood temperature must exceed a certain minimum, preferably in the range from 0.12 to 0.25 degree Centigrade. The amount of the drop may be selected according to the particular patient. The maximum limit selected for this criterion should be less, and may be considerably less, than the totally observed typical extent of the temperature drop at the commencement of physical stress.

3. Similarly, the time rate of change of the temperature drop ($\Delta T/\Delta t$) must exceed a predetermined threshold slope, preferably in the range from 0.12 to 0.20 degree C. per minute, which also may be tailored to the individual patient. This slope of the drop should be less than what the patient would experience at the start of exercise, but greater than a time rate of decrease of blood temperature that might occur when the patient is in a resting state, attributable for example to the individual's circadian rhythm.

4. The heart rate of the patient, and thus the stimulation rate of the pacemaker, must not exceed a predetermined threshold value; preferably, a threshold of 85 beats per minute (bpm). This criterion assures that if the pacing rate control has just been shifted from an exercise function to the reference (resting) function, but at a somewhat higher temperature along the latter curve (which would correspond to a relatively higher heart rate than the threshold rate), the exercise onset-triggered elevation of stimulation rate will not be initiated falsely by the fulfillment of the other criteria and a concurrent temperature drop arising from a different cause, such as respiration-induced drop of the blood temperature. This criterion also avoids false successive and repetitive triggerings of an increased heart rate in such situations.

According to the invention, the fulfillment of all of these criteria is interpreted by the rate-adaptive apparatus of the cardiac pacemaker as indicative of the commencement of exercise by the patient. Thereupon, the stimulation rate of the pacemaker is selectively increased by an amount, for example, 15 bpm, that may be tailored to the particular patient, and that higher rate is maintained for a predetermined period of time, for example, about two minutes, that may be somewhat longer than the duration of the temperature drop at commencement of exercise typically observed in healthy persons with normally functioning hearts. Following the initial temperature drop, the ongoing exercise causes the central venous blood temperature to rise, and the rate-adaptive circuit of the cardiac pacemaker shifts control of the stimulation rate according to the applicable exercise function.

Pacing control commensurate with an exercise function, following the compensatory rate adjustment for the exercise onset-induced temperature dip, may be achieved in any of several different ways. For example, control according to an exercise function may be undertaken only after a predetermined time interval has elapsed with the stimulation rate at an elevated level relative to the resting function curve, at which time the compensatory rate control is discontinued and, following a slight drop in the heart rate, control is resumed according to the first intersected exercise function in the direction of the drop. An alternative method is to maintain the compensatory rate increase after the shift of stimulus rate control from the resting function to an exercise function, coincident with the detection of exercise-induced temperature rise. In the latter alternative, an immediate transition is made from the predetermined rate along the reference (resting) function curve to the corresponding rate along the exercise function curve. As will be seen from the ensuing detailed description of the preferred embodiment, this control parallels the exercise function which would have assumed control had the compensatory rate not been instituted at the incidence of the temperature dip, and therefore constitutes a continuing reaction to the beginning of exercise.

Accordingly, the present invention constitutes an improvement in cardiac pacemakers of the type for adaptively varying the heart rate of a patient based on the blood temperature level according to whether the patient is resting or undergoing exercise. This improvement comprises, within the pacemaker apparatus, means recognitive of and responsive to a drop in the patient's blood temperature exceeding a predetermined miminum within a predetermined time interval from a resting state in which the patient's heart rate is less than a predetermined threshold rate, as indicative of the commencement of exercise by the patient, and for thereupon rapidly increasing the rate at which the patient's heart is stimulated by the pacemaker.

The invention thus provides a method and means to distinguish the initial temperature drop of the central venous blood at the commencement of exercise by the patient, from such other decreases of blood temperature as that naturally occurring after the cessation of physical exercise, or the slower fluctuations (typically, up to 0.5 degree C. over a period of several hours) occurring during night sleep as part of the circadian rhythm, or the smaller respiration-dependent temperature fluctuations. The latter fluctuations are the result of the phasic variations of the blood temperature, especially following exercise, corresponding to the respiration-dependent mixture of warm blood coming from internal organs with a high metabolic rate and high blood temperature, such as liver, spleen and kidneys, with colder blood from the peripheral circulation.

A cardiac pacemaker according to the present invention reacts considerably faster and with greater sensitivity to patient exercise, especially to brief periods of physical activity, in which heat generated by the working muscles and cooler blood circulating to the heart from the extremities have not yet resulted in a state of balance of the central venous blood temperature, after which continued physical exertion will produce an immediate and corresponding rise in the blood temperature.

BRIEF DESCRIPTION OF THE DRAWINGS

The above and still further objects, features, aspects and advantages of the present invention will become apparent to those skilled in the field to which the invention pertains from a consideration of the following detailed description of a preferred embodiment, taken in conjunction with the accompanying drawings, in which.

DETAILED DESCRIPTION OF THE PREFERRED EMBODIMENT

Figure 1:
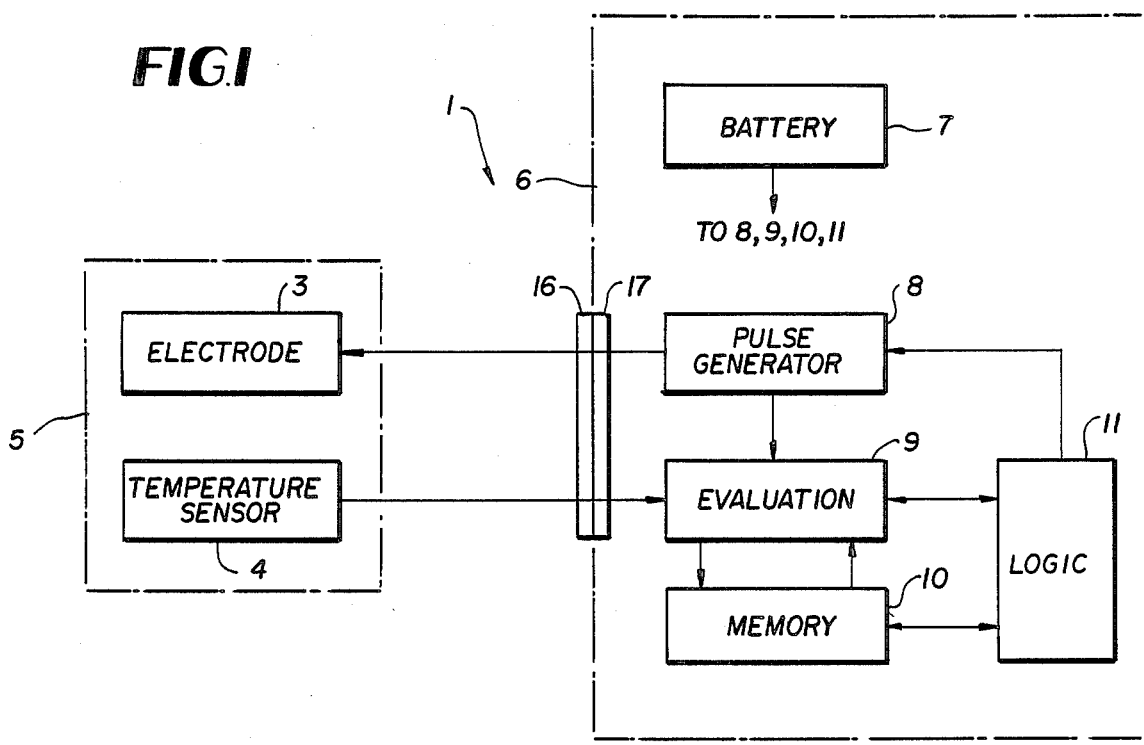
FIG. 1 is a simplified block diagram of a cardiac pacemaker according to the invention.

Referring now to FIG. 1, a cardiac pacemaker 1 has a basic structure corresponding to that described in the aforementioned copending Alt application, the specification of which is hereby incorporated into the instant specification by reference, the pacemaker of the present invention differing only in those respects as will become clear from the ensuing description. For the sake of convenience, the basic structure will be described briefly. Pacemaker 1 has a catheter lead incorporating a pacing electrode 3 and a temperature sensor 4, the sensor being arranged within the lead at a point from about four centimeters to about eight centimeters back from the stimulating tip of the pacing electrode.

The lead is inserted intravenously to place the stimulating electrode tip in proper position within the selected chamber (atrium or ventricle) in the right side of the patient's heart 5. The spacing of the temperature sensor relative to the stimulating tip assures that the sensor will be at or near the boundary between the atrium and the ventricle, and thus at a good mixing point of the central venous blood. The lead is connected at its proximate end to the pacemaker circuitry housed within a case 6, via a male-female connector pair diagrammatically represented by blocks 16, 17. In practice, that portion of the pacemaker housed within case 6, and typically referred to simply (albeit somewhat incompletely) as the stimulus generator or pulse generator, is implanted subcutaneously in a pouch formed by an incision just beneath the skin in the patient's chest.

Case 6 houses a battery 7 which powers other components within the case, including pulse generator 8, analysis or evaluation circuit 9, memory 10, and logic circuit 11. Components 9, 10 and 11 comprise a pacing rate-adaptive circuit by which the stimulation rate of the pacemaker is adaptively varied according to the patient's central venous blood temperature and depending on whether the patient is then physically active or inactive, as described in detail in the copending Alt application. For present purposes it is sufficient to note that the instantaneous level of the central venous blood temperature measured by sensor 4 is sampled at intervals of every few seconds or milliseconds, under the control of logic circuit 11, and the sampled temperature values are received by analysis circuit 9 and stored in memory 10, from which the analysis circuit calculates the time rate of change of the blood temperature. A determination is made by the analysis circuit of whether the patient is then at rest or undergoing exercise, based on a predetermined threshold rate of change of temperature. In response to that determination the logic circuit exercises the appropriate control over the pulse repetition frequency of the pulse generator, and thus, over the rate at which electrical stimuli are delivered to excitable cardiac tissue via the stimulating electrode, with reference to the blood temperature. Analysis circuit 9 and memory 10 are coupled to logic circuit 11 through bidirectional data lines. The sampling rate of instantaneous blood temperature should be at a time interval considerably less than the time interval of the rate of change of blood temperature used for the rest/exercise criterion.

The manner in which the logic circuit controls the pulse generator may be explained by reference to FIG. 2. A basic reference curve K2 represents an idealized heart rate HF as a function of central venous blood temperature T, corresponding substantially to that relationship observed in the typical healthy person having a normally functioning heart and in a state and metabolic condition of non-exercise, at least over the range of heart rates and blood temperatures within the region defined by FIG. 2. This idealized resting curve is linear, indeed essentially a straight line over a range of blood temperatures from $T_{min}=36°$ C. to $T_{max}=40°$ C., in which the heart rate varies from about 50 bpm at the lower end of the curve to about 120 bpm at the higher end.

Figure 2:
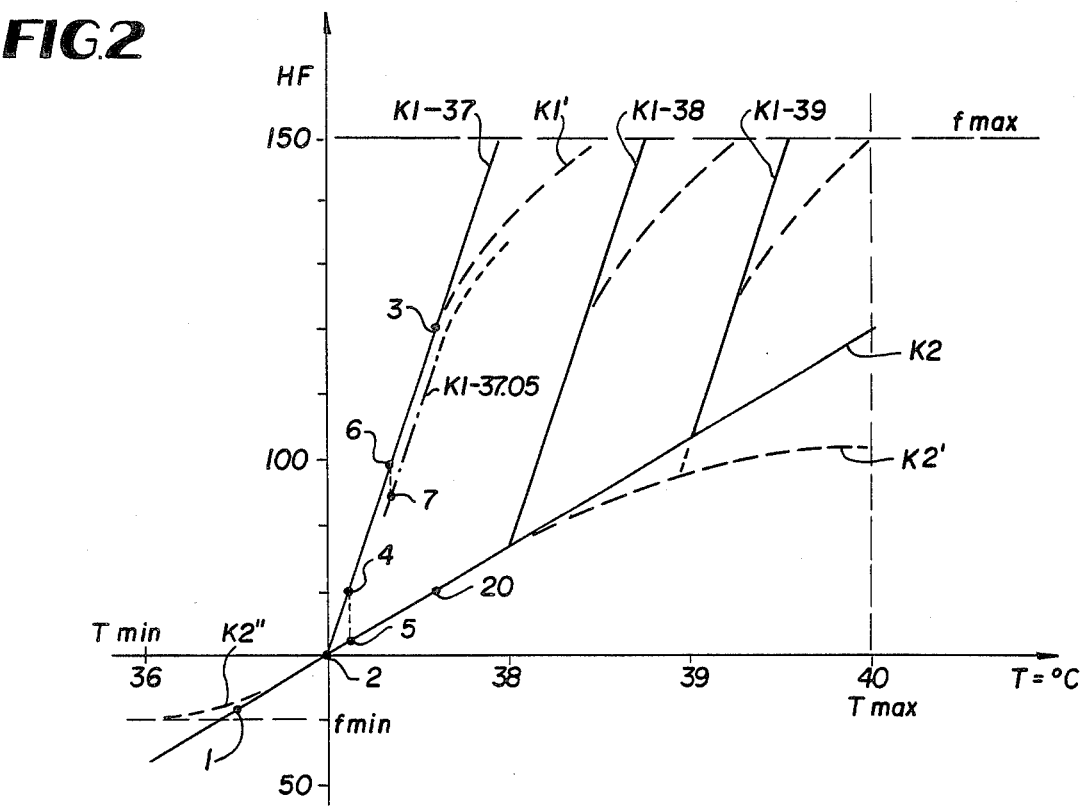
FIG. 2 is a graph illustrating a set of curves representing heart rate as a function of central venous blood temperature under conditions of rest and exercise, for use in controlling the stimulation rate of a cardiac pacemaker.

Symbolically superimposed on the reference (resting) curve in FIG. 2 are exercise curves or functions K1, each of identical slope (about 80 bpm per ° C. for the solid line portions) considerably greater than the slope (about 15 bpm per ° C. for the solid line portion) of the resting function K2. It will be observed that each exercise curve starts at a different working point along the baseline represented by curve K2. For example, the exercise curve K1-37 commences at an absolute temperature of 37° C., relating to a pacing rate of 70 bpm, on the resting baseline. Three exercise functions K1-37, K1-38, K1-39 are symbolically illustrated in FIG. 2, but it will be understood that an exercise curve starts from virtually every point on the resting (baseline) curve, and all of the exercise curves are parallel to one another, i.e., have the same slope. The baseline K2 relates absolute temperature values to heart rates to control the stimulation rate accordingly when the patient is in a non-exercise state, the working point of the rate-adaptive system moving (back and forth) along that baseline consistent with the absolute blood temperature values measured by sensor 4. As that working point moves, the stimulation rate changes. Thus, for example, it will be observed that a three degree change along curve K2 (the solid line portion), say from 37° to 40° C., relates to a 45 bpm change in stimulation rate, from 70 to 115 bpm.

However, once the predetermined criterion (threshold slope) for time rate of change of temperature is met, stimulation rate is adjusted according to the steeper exercise curve K1 starting at the instantaneous absolute temperature on resting curve K2 at which that criterion is met. As noted above, this can occur at virtually any and all points along the resting baseline.

It will also be observed that each of the curves (basic and exercise) may have a diminished slope (represented by the respective dotted line portion) at the end thereof associated with the higher temperature. In the case of an exercise curve, for example, the steeper slope is at the portion along which the working point moves at the start of exercise, and the diminished slope is in the region of continuing exercise. This form of the curve compensates for the slow increase of blood temperature at the start of exercise, as the cooler blood begins to warm at the site of the working musculature, and the faster increase of blood temperature as exercise continues, despite a similar level of exercise at both times. The compensation produces a desirable, almost straight line relationship between relative changes of blood temperature and stimulation rate.

The copending Alt application describes in greater detail the manner in which these functions representing the relationship between heart rate and blood temperature in the resting and exercise states are utilized to control the stimulation rate of the pacemaker. The rate-adaptive circuit continuously determines the temporal change of the central venous blood temperature from the current and previous sampled temperature values measured by the temperature sensor. The working point for each curve (baseline and exercise) in terms of temperature value and stimulation rate, as well as the time rates of change (relative values) of temperature and the measured absolute temperature values are all stored in memory 10. If the time rate of change of the blood temperature does not exceed the predetermined threshold value representing the criterion for determining when the patient goes from a resting to an exercise state, the logic circuit controls the variation or adjustment of stimulation rate in accordance with the resting function K2. Once the time rate of change of blood temperature exceeds the predetermined threshold value, the logic circuit shifts the working point, and thereby, the control of stimulation rate to an exercise function K1 starting at that instantaneous measurement of absolute blood temperature value along curve K2. In the opposite direction, that is, when the time rate of change of blood temperature over a predetermined period of time indicates that the working point should no longer continue along the exercise curve, or a state of balance (a steady state) exists between periods of exercise, the system returns the working point toward the basic curve K2.

Figure 3:
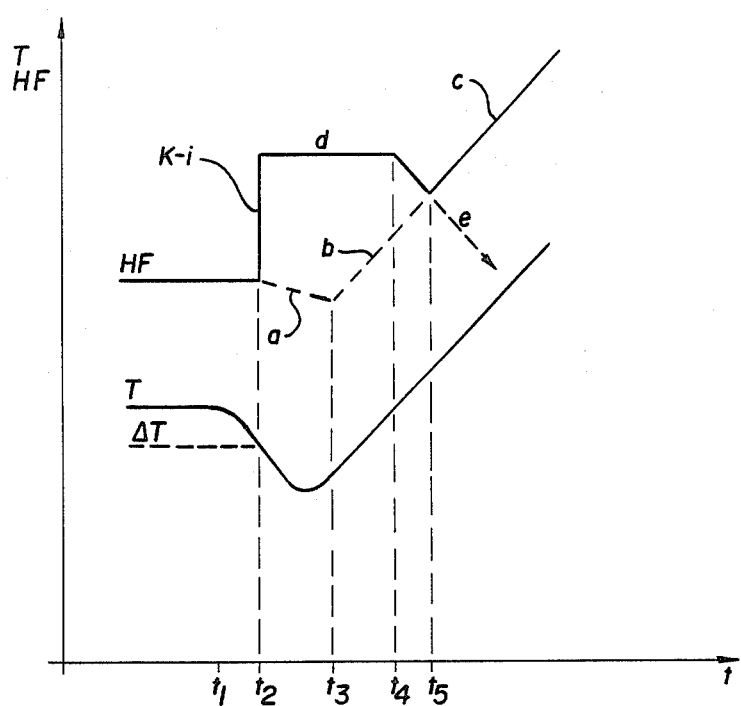
FIG. 3 is a graph illustrating the relative variations of the central venous blood temperature and of the stimulation rate (and thus, the heart rate) with time as the pacemaker patient commences physical exertion, useful for describing the manner in which the cardiac pacemaker is controlled during that period according to the invention.

Curves illustrating central venous blood temperature T and heart rate (and stimulation rate) HF as functions of time over a period from immediately before to shortly after the commencement of exercise by the pacemaker patient, are shown in FIG. 3. Initially, the patient is in a resting state, i.e., essentially inactive physically. If there are no transitory effects from recent physical activity, the patient's central venous blood temperature is substantially constant at that time. Similarly, his heart rate is virtually constant, the pacemaker stimulation rate being controlled according to the resting function K2 (FIG. 2).

At time $t_1$, the patient commences physical activity, such as leaving a seated position and walking out of the room. At the inception of this activity, his central venous blood temperature begins to drop, for reasons discussed above. Within a brief interval thereafter, at time $t_2$, the rate-adaptive circuit described in the copending Alt application would respond to this temperature drop by initiating a slight reduction in the pacing rate pursuant to control according to the resting function K2. Such rate reduction is illustrated by the dashed line labeled a in the curve of the heart rate HF. As explained earlier, after a short time the blood temperature T begins to rise as a result of the continuing exercise. At time $t_3$, that rate-adaptive circuit would respond to the rapidly rising temperature by shifting control of the pacing rate from the resting function K2 to the appropriate exercise function K1, as indicated by the dashed line b of the HF curve. The stimulation rate of the pacemaker would remain under the control of the exercise function along the portions b and c of curve HF as blood temperature T continues to climb.

According to the preferred embodiment of the present invention, however, the rate-adaptive circuit of the pacemaker is implemented to respond differently to the initial temperature drop, subject to the fulfillment of the criteria indicative of onset of exercise, as described above. In particular, based on the assumption in the immediately preceding example that the patient is initially in a state of rest and not a condition of recovery from a preceding physical exertion, up to time $t_1$ the stimulation rate of the pacemaker is still controlled according to the resting function curve K2. Assume further that the patient's heart rate is then below the predetermined threshold rate of 85 bpm, as would normally be the case under these conditions unless his blood temperature were significantly elevated because of, say, a fever. The pacing rate remains controlled according to resting curve K2 until, at time $t_2$, the other essential criteria are met as a consequence of the blood temperature having dropped by an absolute amount equal to $\Delta T$ within a time interval $\Delta t$, where $\Delta T$ exceeds the predetermined minimum dropp and $\Delta T/\Delta t$ exceeds the threshold slope of the drop.

Logic circuit 11 recognizes the fulfillment of the criteria relating to resting function and heart rate, and in conjunction with analysis circuit 9, temperature sensor 4 and memory 10, recognizes the meeting of the other criteria relating to the extent and the slope of the blood temperature drop as being indicative of the inception of physical exercise. In response, at time $t_2$ the logic circuit initiates a rapid compensatory increase of, for example, about 15 bpm in the pacing rate by controlling the output frequency of pulse generator 8 according to an initial characteristic curve K-i (FIG. 3) of heart rate HF.

The stimulation rate is maintained at that increased rate level, as indicated by the horizontal line d, for a predetermined time interval. At the conclusion of that interval, the logic circuit causes the pulse generator to reduce the stimulation rate in the direction of the original value, indicated by the partial broken line e in the graph of FIG. 3. The point at which the rate changes from line d to line e is at time $t_4$, and it will be observed from FIG. 3 that the time interval over which the increased rate is manifested is somewhat greater than the duration of the blood temperature dip, in the illustrative embodiment whose operation is exemplified by that graph. Lines d and e in their entirety constitute initial characteristic function K-i, according to which the cardiac pacing rate is controlled at the beginning of physical exercise in recognition of and response to the exercise onset-induced blood temperature dip. Rate control according to function K-i continues until a point in time $t_5$, at which the function line K-i intersects the broken line b. It will be recalled from the above description of operation of the rate adaptive circuit disclosed in the copending Alt application, without the improvements according to the present invention, that circuit would have controlled the stimulation rate along the path of lines a and b in response to the drop in blood temperature reflected by the curve T. According to the present invention, at the intersection of the lines K-i and b, rate control is shifted (by the logic circuit) from the K-i function of heart rate to the appropriate exercise function K1 representing the relationship between heart rate and blood temperature during physical exercise. Hence, the curve of heart rate HF now follows the line c. It will be apparent from FIG. 3 that the heart rate and the blood temperature curves are nearly synchronous in this range.

Figure 4:
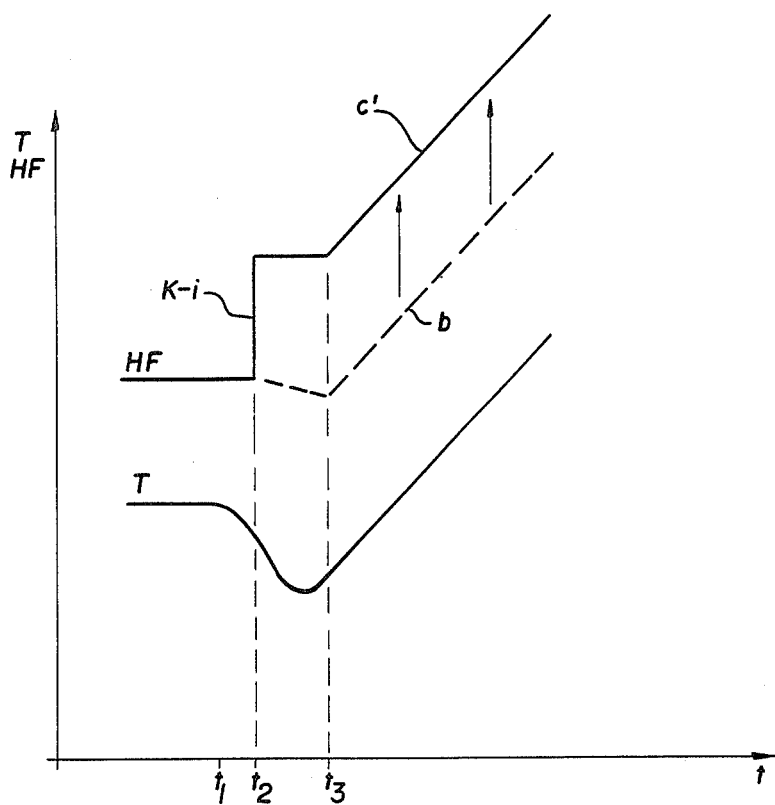
FIG. 4 is a graph similar to that of FIG. 3, illustrating time rates of change of blood temperature and stimulation rate (heart rate) for another method of control at the commencement of exercise.

Referring now to FIG. 4, the same curve of the central venous blood temperature T over time t is shown as is shown in FIG. 3, with an alternative method for shifting control of the stimulation rate from the compensatory increased rate (initial characteristic function of heart rate) in recognition of and response to the commencement of exercise, to an appropriate exercise function. Here again, an initial body exercise is assumed to have been detected at time $t_2$, based on the fulfillment of the fundamental criteria described above. Thus, the logic circuit exerts control over the pulse generator to adjust the rate at which stimuli are delivered by the pacemaker, according to the initial characteristic function line K-i, in the same manner as described above in connection with the method of FIG. 3.

In the alternative technique of FIG. 4, at time $t_3$ the logic circuit recognizes that the stimulation rate is to be switched to adjustment according to an exercise characteristic function, represented by the broken line b of the heart rate curve HF. Here, instead of reverting back toward the original rate, the elevated pacing rate is maintained by shifting the rate control along a path c', corresponding to a parallel thrust of line b, at the point of intersection of c' with function K-i. As the patient continues to exercise, the pacing rate is controlled according to the exercise function represented by the path c'. This also preserves synchronism between the blood temperature T and the heart rate HF, but in this case the heart rate is more sharply accentuated.

Although a preferred embodiment and method have been described, other forms contemplated by the invention will be apparent to the skilled practitioner. For example, the shape of the initial characteristic function K-i in FIGS. 3 and 4 is purely illustrative, other physiologically well-tolerated rate increases being usable. Accordingly, the invention is to be limited only by the appended claims.

We claim:

1. A rate-responsive cardiac pacemaker, comprising
    means for sensing the central venous blood temperature of the patient,
    means responsive to the sensed blood temperature for detecting the onset of exercise by the patient by recognition of the characteristic drop in blood temperature associated therewith, and adjusting means responsive to detection of the onset of exercise for thereupon stepping up the stimulation rate of the pacemaker.

2. The pacemaker of claim 1, in which said detecting means is adapted to recognize said characteristic drop by applying at least two of the criteria from the group including (i) occurrence of the temperature drop at a point in time at which the patient has been at rest, (ii) occurrence of the temperature drop at a point in time at which the patient's heart rate is below a threshold rate indicative of recently completed exercise, (iii) magnitude of the temperature drop exceeds a predetermined minimum amount, and (iv) time rate of change of the temperature drop is within a predetermined range of values between a value indicative of recently completed exercise and a value indicative of a change associated with the patient's circadian rhythm.

3. The pacemaker of claim 2, in which said threshold heart rate is equal to or greater than 85 beats per minute, said predetermined minimum amount of the temperature drop is in the range of 0.12 to 0.25 degree C., and said predetermined range of values is from 0.12 to 0.2 degrees C. per minute.

4. The pacemaker of claim 1, in which said adjusting means includes means for maintaining the stimulation rate at the stepped up level for a predetermined period of time at least equal to the duration of the recognized temperature drop.

5. The pacemaker of claim 4, in which said adjusting means further includes means for controlling the stimulation rate after said predetermined period of time according to an algorithm designating stimulation rate as a function of blood temperature characteristic of a condition of exercise, for the period of continuing exercise.

6. A stimulus generator for a temperature driven rate responsive cardiac pacemaker, comprising means responsive to the temperature of the central venous blood of the patient for detecting the onset of exercise by the patient by recognition of the characteristic drop in blood temperature associated therewith, means responsive to the metabolic state of the patient for distinguishing said characteristic drop in blood temperature from decreases of the blood temperature attributable to other causes, and adjusting means responsive to detection of the onset of exercise for abruptly increasing the stimulation rate of the generator.

7. The stimulus generator according to claim 6, in which said detecting means is adapted to recognize said characteristic temperature drop by applying at least one of the criteria from the group including (i) magnitude of the temperature drop exceeds a predetermined minimum amount, and (ii) time rate of change of the temperature drop exceeds a predetermined minimum value.

8. The stimulus generator according to claim 7, in which said distributing means is adapted to discriminate said characteristic temperature drop from decreases of the blood temperature attributable to other causes by applying at least one of the criteria from the group including (i) commencement of the temperature drop at a point in time at which the stimulation rate of the generator is controlled according to an algorithm designating stimulation rate as a function of blood temperature for a metabolic state indicative of physical inactivity of the patient, and (ii) at said point in time the patient's heart rate is below a threshold rate for a metabolic state indicative of recent exercise.

9. The stimulus generator according to claim 6, in which said adjusting means includes means for maintaining the stimulation rate at the increased rate level for a period of time at least equal to the period of the temperature drop.

10. The stimulus generator according to claim 9, in which said adjusting means further includes means for controlling the stimulation rate after said period of time according to a predetermined algorithm designating stimulation rate as a function of blood temperature characteristic of a condition of exercise, for the duration of the exercise period.

11. The stimulus generator according to claim 6, in which said adjusting means includes means for maintaining the stimulation rate at an increased rate level for a predetermined period of time, and means responsive to the conclusion of said period of time for returning the stimulation rate toward the rate existing immediately prior to detection of the onset of exercise and responsive to continuing exercise by the patient to interrupt said return and thereupon control the stimulation rate according to a predetermined algorithm designating stimulation rate as a function of blood temperature characteristic of a condition of exercise.

12. In an implantable cardiac pacemaker for adaptively varying the heart rate of a patient based on the level of the patient's central venous blood temperature, the improvement comprising means for detecting a drop of predetermined extent and duration in the blood temperature from a time when the patient is in a resting state, as indicative of the commencement of physical activity by the patient, and means responsive to said detection for rapidly increasing the stimulation rate of the pacemaker in an amount and for a time commensurate with physiological response to the commencement of exercise in a healthy person with a normally functioning heart.

13. An exercise responsive cardiac pacemaker, comprising means for controllably varying the stimulation rate of the pacemaker according to whether the patient is at rest or undergoing exercise, based on the instantaneous level of the patient's blood temperature, and means responsive to a relatively rapid drop in the patient's blood temperature commencing from an apparent state of rest of the patient, as indicating commencement of exercise by the patient, and for thereupon increasing the stimulation rate to a level consistent with exercise.

14. A cardiac pacemaker including a control means for automatic adaptation of the stimulation rate of the pacemaker to the metabolic state of the patient, said control means comprising a temperature sensor for detecting the central venous blood temperature of the patient, said sensor disposed for introduction into a preselected chamber of the right side of the patient's heart, and circuit means connected to the sensor for controlling said stimulation rate, said circuit means including means responsive to a preselected physiological parameter indicative of metabolic state of the patient for determining therefrom whether the patient is then at rest or undergoing exercise, means executing separate algorithms defining stimulation rate as a function of blood temperature for rest state and exercise state of the patient, respectively, and responsive to said determination and to the detected blood temperature for regulating said stimulation rate according to the respective algorithm representative of the determined state of the patient, and means responsive to the coincidence of (i) said stimulation rate being regulated according to one of said algorithms representative of the rest state of the patient, (ii) the then-current stimulation rate being less than a predetermined value, and (iii) a drop in the detected blood temperature exceeding a predetermined minimum amount within a predetermined time interval, for thereupon increasing the stimulation rate by a preset amount.

15. The cardiac pacemaker according to claim 14, wherein said determining means is responsive to the time rate of change of the patient's blood temperature relative to a preselected threshold value, said predetermined physiological parameter being blood temperature, as indicative of a rest state when the time rate of change of blood temperature is below said threshold value and as indicative of an exercise state when the time rate of change of blood temperature exceeds said threshold value.

16. The cardiac pacemaker according to claim 15, wherein said regulating means is responsive to the time rate of change of blood temperature exceeding said threshold value following said drop in the detected blood temperature, for regulating said stimulation rate according to one of said algorithms representative of the exercise state of the patient at the moment when the stimulation rate according to the last-mentioned algorithm reaches a predetermined rate relative to the increased rate.

17. The cardiac pacemaker according to claim 14, wherein said increased stimulation rate is maintained for a predetermined period of time.

18. A method for adaptively regulating an exercise responsive cardiac pacemaker in which the stimulation rate is based on the central venous blood temperature of the patient according to whether the patient is resting or undergoing exercise, said method comprising detecting a drop in the blood temperature exceeding a predetermined amount within a predetermined time interval, at a time when the patient is in an apparent state of rest with a heart rate not exceeding a predetermined threshold rate, treating such detected temperature drop as denoting the onset of exercise by the patient, and abruptly increasing the stimulation rate to a rate consistent with that of a healthy person with a normal functioning heart, coincident with such detection.

* * * * *

UNITED STATES PATENT AND TRADEMARK OFFICE
CERTIFICATE OF CORRECTION

PATENT NO. : 4,719,920

DATED : January 19, 1988

INVENTOR(S) : Eckhard Alt, et al.

It is certified that error appears in the above-identified patent and that said Letters Patent is hereby corrected as shown below:

Col. 2, line 43, delete "The heart temperature" and insert --The temperature--.

Col. 3, line 66, delete "whetCher" and insert --whether--.

Col. 9, line 45, delete "dropp" and insert --drop--.

Col. 11, line 66 (Claim 8), delete "distributing" and insert --distinguishing--.

Signed and Sealed this

Twelfth Day of July, 1988

Attest:

DONALD J. QUIGG

*Attesting Officer*    *Commissioner of Patents and Trademarks*

REEXAMINATION CERTIFICATE (1206th)
United States Patent [19]
Alt et al.

[11] B1 4,719,920
[45] Certificate Issued  Feb. 13, 1990

[54] EXERCISE-RESPONSIVE RATE-ADAPTIVE CARDIAC PACEMAKER

[75] Inventors: Eckhard Alt, Munich, Fed. Rep. of Germany Richard Calfee

[73] Assignee: Intermedics, Inc., Angleton, Tex.

Reexamination Request:
No. 90/001,662, Dec. 8, 1988

Reexamination Certificate for:
Patent No.: 4,719,920
Issued: Jan. 19, 1988
Appl. No.: 917,558
Filed: Oct. 10, 1986

[51] Int. Cl.⁴ .............................................. A61N 1/36
[52] U.S. Cl. .............................. 128/419 PG; 128/736
[58] Field of Search ......................... 128/419 PG, 736

[56] References Cited
U.S. PATENT DOCUMENTS
4,436,092  3/1984  Cook et al. .................. 128/419 PG

OTHER PUBLICATIONS

Axel Laczkovics, "The Central Venous Blood Temperature as a Guide For Rate Control in Pacemaker Therapy" PACE, vol. 7, pp. 822–830, Sep.–Oct., 1984.
N. E. Fearnot, et al., "Increasing Cardiac Rate by Measurement of Right Ventricular Temperature" (Poster) RBM–Revue Europeanne de Technologie Biomedicale, vol. 6, No. 3, p. 266, 1984.
David Jolgren, et al, "A Rate-Responsive Pacemaker Controlled by Right Ventricular Blood Temperature" PACE, vol. 7, Part V, pp. 794–801, Sep.–Oct., 1984.
T. Duncan Sellers, et al, "Central Venous Temperature Profiles for a Pacemaker Algorithm" (NASPE Abstract No. 27) PACE, vol. 8, p. 294, Mar.–Apr., 1985.

Poster presented at North American Society of Pacing and Electrophysiology (NASPE) on May 9–11, 1985.
T. Duncan Sellers, et al., Brochure entitled: "Central Venous Temperature Profiles For a Pacemaker Algorithm", Distributed at North American Society of Pacing and Electrophysiology (NASPE) Meeting on May 9–11, 1985.
Alt, et al., "Zemtralvenose Bluttemperatur als Regelgrosse der Schrittmacherfrequenz", Herzschrittmacher 5 (1985) Nr. 2, pp. 66–71, (Published May 17, 1985).
T. Duncan Sellers, et al., "Right Ventricular Blood Temperature Profiles for a Physiologic Pacing" (American Heart Association abstract), Circulation, vol. 72, (Suppl. III), p. 1730, 1985.
Graph presented at the American Heart Association Meeting, Nov. 10–13, in 1985, the Cook Pacemaker booth.

Primary Examiner—William E. Kamm

[57] ABSTRACT

A temperature driven rate responsive cardiac pacemaker adapted to distinguish between physiologically determined changes of the patient's blood temperature under conditions of exercise and non-exercise, and to adaptively vary the rate at which stimuli are generated accordingly, is also capable of recognizing the blood temperature dip which is characteristic of the commencement of exercise. In response to such a temperature dip, the pacemaker initiates a rapid and physiologically beneficial increase in the stimulation rate. To assure the proper selective initiation of a rate increase, the pacemaker discriminates between a blood temperature drop indicative of the onset of exercise and those temperature drops which occur for other reasons, such as upon cessation of exercise or as normal phasic variations, including respiration and circadian fluctuations.

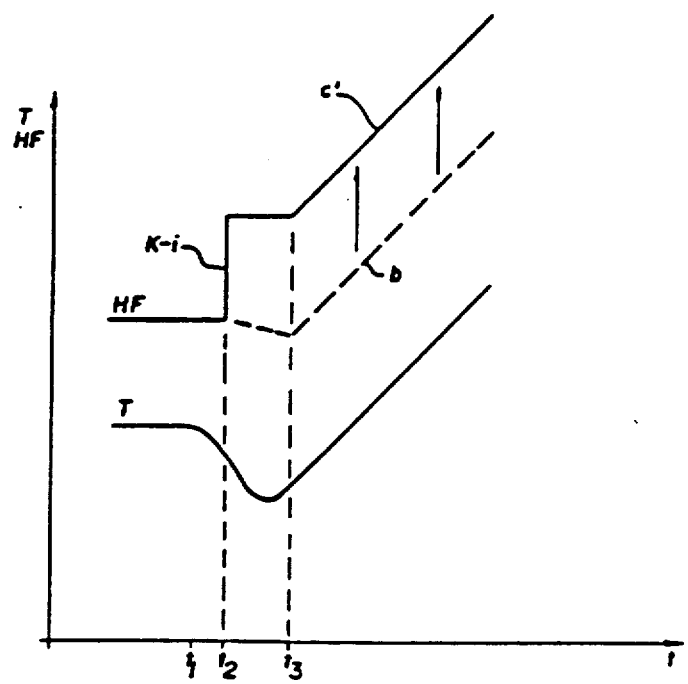

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claims 1-18 is confirmed.

* * * * *